United States Patent [19]

Gerson et al.

[11] Patent Number: 4,737,492

[45] Date of Patent: Apr. 12, 1988

[54] SPARINGLY SOLUBLE SALTS OF CEFAMANDOLE, AND OPHTHALMIC COMPOSITIONS CONTAINING SAME

[75] Inventors: Steven H. Gerson; Wesley W. Han, both of Fort Worth, Tex.

[73] Assignee: Alcon Laboratories, Inc., Fort Worth, Tex.

[21] Appl. No.: 948,182

[22] Filed: Dec. 31, 1986

[51] Int. Cl.[4] .................. A61K 31/545; C07D 501/36
[52] U.S. Cl. ...................................... 514/204; 540/226
[58] Field of Search ................ 540/226, 227; 514/204

[56] References Cited

U.S. PATENT DOCUMENTS

| 2,627,491 | 2/1953 | Szabo et al. | 514/199 |
| 2,812,326 | 11/1957 | De Rose | 540/323 |
| 3,641,021 | 2/1972 | Ryan | 540/227 |
| 4,529,720 | 7/1985 | Cole et al. | 514/210 X |

Primary Examiner—Donald G. Daus
Assistant Examiner—William A. Teoli, Jr.
Attorney, Agent, or Firm—James A. Arno; Gregg C. Brown

[57] ABSTRACT

The hydrabamine and benzathine salts of cefamandole are useful in aqueous ophthalmic compositions which have good stability and shelf life.

7 Claims, No Drawings

SPARINGLY SOLUBLE SALTS OF CEFAMANDOLE, AND OPHTHALMIC COMPOSITIONS CONTAINING SAME

BACKGROUND OF THE INVENTION

1. Field of the Invention

The present invention relates to salts of cefamandole, a member of the cephalosporin family of antibiotics. This invention also relates to compositions containing the salts, and to methods of making and using those compositions. The salts have a very limited aqueous solubility, and therefore can be formulated in aqueous compositions having long term stability.

2. Discussion of Related Art

Cefamandole is a semisynthetic cephalosporin antibiotic presently in use as a parenterally administered drug. This drug is described in U.S. Pat. No. 3,641,021. During the developmental phase of this drug, it was found that cefamandole is very difficult to crystallize. Subsequently, a formic acid ester of cefamandole called cefamandole nafate was developed as a prodrug. The sodium salt of that ester is now marketed under the trade name of Mandol. The nafate ester of cefamandole is considered to be undesirable for topical ophthalmic administration because it is more unstable than the parent molecule and one of its degradation products, formic acid, is a potential source of ocular irritation.

When placed in an aqueous environment, cefamandole is subject to hydrolysis through several parallel mechanisms. The kinetics of that degradation have been thoroughly investigated in the prior art. For example, under the most favorable of conditions for an aqueous solution, cefamandole is degraded by 10% after 2.2 days at room temperature. This degradation is highly temperature dependent, meaning that a slight fluctuation in temperature above room temperature can accelerate the decomposition of an already very unstable molecule. It has been determined that in order to prepare a viable preparation for ophthalmic administration, the rate of decomposition must be decreased by at least three hundred fold.

Several mechanisms to stabilize cefamandole exist. One such method is the utilization of the principle of a sparingly water soluble salt. Theoretically, for a sparingly water soluble salt, only those molecules that are dissolved in water are susceptible to water attack, and as the solubilized drug is degraded more drug will dissolve to maintain the equilibrium solubility. The net effect is that the rate of degradation is dependent on the solubility of the molecule, and not on the total amount of drug. Thus, the reaction is said to be zero order. Mathematically, the rate of decomposition for a sparingly water soluble salt is given as:

$$(dc/dt) = -K(C) = -KS = K_o,$$

where the rate of decomposition, $dc/dt$, is proportional to the concentration $C$ in solution, which is the solubility, $S$; and $K_o$ is a zero order reaction constant.

For an aqueous ophthalmic preparation of 0.5% concentration to be stable for two years at room temperature, the $K_o$ must be be $6.84 \times 10^{-7}$ gram per milliliter per day. Since it is known that the hydrolysis rate constant K is 0.046 per day at room temperature, it follows that the required solubility of the sparingly water soluble salt must be $1.48 \times 10^{-5}$ gram per milliliter or less.

Penicillin V is a classic example of a compound susceptible to hydrolysis similar to the cephalosporins and having comparable stability problems. To overcome these stability problems, benzathine and hydrabamine salts prepared as the sparingly water soluble molecule are known in the art. See U.S. Pat. Nos. 2,812,326 and 2,627,491. The use of such benzathine or hydrabamine salts for cephalosporins to overcome this stability problem is not known in the prior art.

SUMMARY OF THE INVENTION

It is an object of this invention to provide novel salts for cephalosporin antibiotics for use as an ophthalmic medication.

It is a further object of this invention to provide stable salts of these cephalosporins which will not readily dissolve in an aqueous environment.

It is a still further object of this invention to provide a crystalline structure improved over cefamandole.

It is an even further object of this invention to provide the sparingly soluble salts with sustained release action.

It is another object of this invention to avoid the use of a nonaqueous vehicle and thus avoid the ocular discomfort caused by the use of such nonaqueous vehicle.

Another object of this invention is to provide compositions containing the sparingly soluble salts for use as ophthalmic medications.

It is yet a further object of this invention to provide methods for preparing these compositions to be used as medications.

Other objects and advantages of the invention will become apparent as the description thereof proceeds.

In satisfaction of the foregoing objects, the present invention provides novel cefamandole salts, methods for the preparation of the cefamandole salts, the use of these salts in various ophthalmic suspensions or compositions, and for use of the compositions.

DETAILED DESCRIPTION OF THE INVENTION

The present invention is based on the discovery that benzathine and hydrabamine salts of cefamandole provide cephalosporins in a form which have limited aqueous solubility and as a result increased shelf stability. Since only the dissolved portion of the salt is subject to hydrolysis, the lack of solubility serves to increase the half life of the drug present.

The general class of compounds with which this invention is concerned are salts of cefamandole. This compound has the following formula:

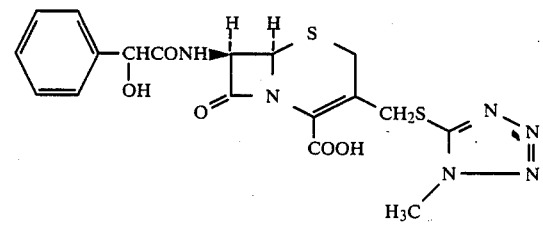

According to this invention, salts of this compound which have good shelf life and are sparingly water soluble are produced by reaction with either hydrabamine or benzathine. Hydrabamine is didehydroabietylamine, a known compound. The hydrabamine salts are preferred. It has been found that these salts provide a desirable stability profile for the cefamandole, provide adequate crystalline structure which is improved over that of cefamandole, provide a compound which will give sustained release action, and avoid uncomfortable, nonaqueous vehicles which are sometimes used for administration of cefamandole.

The hydrabamine salt of cefamandole is prepared by neutralizing hydrabamine hydrochloride with base, extracting the free amine into chloroform, and reacting this solution with a solution of cefamandole acid in ethyl acetate.

The cefamandole benzathine is prepared from the corresponding cefamandole sodium salt by neutralization of the sodium salt by hydrochloric acid and extraction into ethylacetate. After recovery of the free cefamandole acid, it is reacted in ethylacetate with benzathine to produce a salt.

It has been found that these salts of cefamandole provide ophthalmic suspensions or compositions which have good shelf life and which can be administered without having to be made as a fresh solution. The shelf life may range up to two years. Because these salts are hydrophobic, pharmaceutical compositions containing the salts require a surfactant in order to disperse and wet the particles to form a suspension. The presence of a surfactant can increase the solubility of the salts and accelerate the decomposition thereof. The selection of a wetting agent which will not cause any substantial increase in solubility is therefore very important; preferred surfactants are the benzalkonium chlorides.

The following are preferred ophthalmic compositions of the present invention:

| Component | Wt. % |
|---|---|
| Cefamandole salt | 0.1 to 4 |
| Boric Acid | 0.5 to 3 |
| Anhydrous Sodium Sulfate | 0.1 to 0.2 |
| Sodium Chloride | 0.1 to 0.4 |
| Benzalkonium Chloride | 0.1 to 0.5 |
| Sulfuric Acid or Sodium Hydroxide | QS pH 4 to 9 |
| Purified water | QS 100% |

The above compositions may be administered as ophthalmic preparations according to known methods for the administration of cefamandole. With regard to topical, ophthalmic administration by drops, the frequency and duration of treatment is left to the routine determination of the clinician when indicated to combat ophthalmic microbial infection.

The following specific examples will illustrate the preferred methods for making the cefamandole salts of the present invention, as well as their solubility and stability characteristics. These examples should not be construed to limit the invention to the precise proportions employed, nor the specific procedures, and are merely shown to illustrate the inventive concept involved. Parts are by weight unless otherwise indicated.

EXAMPLE 1

This example illustrates the synthesis of cefamandole hydrabamine. To 8.00 grams (0.0287 mol) dehyroabietylamine dissolved in 40 mL xylene was added 1.15 mL (2.51 g, 0.0134 mol) 1, 2 dibromoethane, and 5.2 mL (3.67 g, 0.360 mole) triethylamine, and the resulting solution was refluxed for 15 hours. The triethylamine hydrobromide formed was removed by filtration, thoroughly washed with ether, and the combined filtrate and ether washings were concentrated in vacuuo to give a thick, brown oil. The oil was slurried with two 5 mL portions of methanol and then dissolved in 50 mL of ethanol. Hydrabamine hydrochloride was precipitated by the dropwise addition of 1.0N hydrochloric acid. The crude salt was placed in a soxhlet thimble and was continuously extracted by ether for nine hours. The salt which remained in the thimble was dried in vacuuo at 40° C., and was found to be sufficiently pure for further use.

A suspension of 1.20 g (0.00143 mole) hydrabamine hydrochloride in water was made alkaline by the addition of 1.0N sodium hydroxide and wax extracted with five 10 mL portions of chloroform. The combined organic washings were dried over magnesium sulfate and filtered. A solution of 1.48 g (0.00305 mole) cefamandole sodium dissolved in 10 mL H$_2$O was made acidic by addition of 1.0N hydrochloric acid and extracted three times with 5 ml of ethyl acetate. The combined organic washings were dried over magnesium sulfate and filtered. The chloroform solution was added dropwise with stirring and cooling to the ethyl acetate solution. The cefamandole hydrabamine which precipitated was collected by filtration, washed with ether and dried in vacuuo.

EXAMPLE 2

This example illustrates the synthesis of cefamandole benzathine. A solution of 0.194 grams ($4.0 \times 10^{-4}$ mol) cefamandole sodium in 10 mL of water was placed in a separatory funnel containing 10 mL ethyl acetate. The aqueous phase was acidified with 1.0N hydrochloric acid, and the free cefamandole acid was extracted three times with 10 mL portions of ethyl acetate. The combined organic washings were dried over magnesium sulfate. To the solution of cefamandole and ethyl acetate was added 0.1 mL (2.40 grams, $1.00 \times 10^{-3}$ mol) benzathine. The precipitated cefamandole benzathine was separated by filtration, washed with ether and dried in vacuuo.

What is claimed is:

1. A member selected from the group consisting of cefamandole benzathine and cefamandole hydrabamine.

2. A compound according to claim 1 which is cefamandole hydrabamine.

3. A compound according to claim 1 which is cefamandole benzathine.

4. An ophthalmic antibiotic topical composition comprising a therapeutically effective amount of a sparingly water soluble cefamandole salt selected from cefamandole benzathine and cefamandole hydrabamine in an aqueous vehicle.

5. An aqueous ophthalmic antibiotic topical composition comprising a therapeutically effective amount of a sparingly water soluble cefamandole salt selected from cefamandole benzathine and cefamandole hydrabamine and a surfactant at a pH of from 4.0 to 9.0.

6. A method for treating an ophthalmic condition mediated by a bacterial infection which comprises administration of a pharmaceutical composition of claim 4.

7. A method for treating an ophthalmic condition mediated by a bacterial infection which comprises administration of a pharmaceutical composition of claim 5.

* * * * *